United States Patent
Guns et al.

(10) Patent No.: US 6,589,293 B1
(45) Date of Patent: Jul. 8, 2003

(54) DEPILATORY PAINT THICKENER COMPRISING AN ANYLOPECTIN STARCH

(75) Inventors: Jacobus Guns, Hoogezand (NL); Jacques Lacroix, Evry (FR); Pieter Lykle Buwalda, Groningen (NL)

(73) Assignee: Cooperatieve Verkoop-En Productievereniging Van Aardappelmeel En Derivaten Avebe B.A., Ja Veendam (NL)

( * ) Notice: Subject to any disclaimer, the term of this patent is extended or adjusted under 35 U.S.C. 154(b) by 0 days.

(21) Appl. No.: 09/743,399

(22) PCT Filed: Jul. 19, 1999

(86) PCT No.: PCT/NL99/00461
§ 371 (c)(1),
(2), (4) Date: Mar. 12, 2001

(87) PCT Pub. No.: WO00/05420
PCT Pub. Date: Feb. 3, 2000

(30) Foreign Application Priority Data

Jul. 22, 1998 (EP) .............................................. 98202457

(51) Int. Cl.[7] ................................................. C14C 1/06
(52) U.S. Cl. ........................... 8/94.16; 8/94.1 R; 8/160; 8/161; 8/94.15; 8/94.32; 510/275
(58) Field of Search ........................ 510/275; 8/94.1 R, 8/94.16, 160, 161, 94.15, 94.32

(56) References Cited

U.S. PATENT DOCUMENTS 4,618,344 A  * 10/1986  Wells ............................ 8/161
5,034,221 A  *  7/1991  Rosen et al. ................... 424/73

FOREIGN PATENT DOCUMENTS

| AT | 403 705 B | 5/1998 |
| DE | 622 355 | 6/1938 |
| DE | 3338957 A1 | 5/1985 |
| GB | 923058 | 4/1963 |
| GB | 2 045 278 A | 10/1980 |

OTHER PUBLICATIONS

Vivian, Low lime depilatory paints for sheep skins, Twenty–first Meat Industry Research Conference, pp 102–104, (date unknown).*

"Low–Lime Depilatory Paints For Sheep Skins", by G.W. Vivian, M.S.C., Ph.D., MNZIC, *Twenty–First Meat Industry Research Conference*, at pp. 102–104. date unknown.

* cited by examiner

*Primary Examiner*—Charles Boyer
(74) *Attorney, Agent, or Firm*—Hoffman & Baron, LLP

(57) ABSTRACT

The invention relates to the dehairing (depilating) of animal pelts, hides or skins, more specifically to depilatory paint and depilatory paint (depilation paint) thickener used in the depilation process in for example fellmongeries. The invention provides a depilatory paint thickener comprising a starch containing essentially only amylopectin molecules. Such thickener, is among other things, easily soluble in cold water; improves diffusion of chemicals (like sulfide or lime) throughout the skin; improves viscosity or resistance to shear of a paint, whereby less starch is needed to exert a similar effect; and increases the suspendability of a lime, allowing less time to be used which creates environmental advantages in waste disposal.

14 Claims, No Drawings

DEPILATORY PAINT THICKENER COMPRISING AN ANYLOPECTIN STARCH

This application claims priority based on International Application No. PCT/NL99/00461, filed on Jul. 19, 1999 and EPO Application No. EP 98202457.2, filed on Jul. 22, 1998.

BACKGROUND OF THE INVENTION

The invention relates to the dehairing or dewooling (depilating) of animal pelts, hides or skins, more specifically to depilatory paint and depilatory paint (depilation paint) thickener used in the depilation process in for example fellmongeries.

Depilation is a process whereby a depilatory paint is applied to a (sometimes pre-shorn) hide or skin and let to soak for several hours during which chemicals act to de-hair the skin. During that time, the paint should remain in place to provide for continuous chemical action, for which a certain thickness or viscosity is required. After depilation, the skins or hides (now often called slats) are washed and cleaned for further processing. Depilated hair is in general not further useful, depilated wool (now often called slipe wool) sometimes finds further use.

Traditionally (see depilatory thickeners, S. M. Cooper, New Zealand Leather and Shoe Research Institute) hydrated lime has been used for thickening depilatory paint. It has a number of advantages. It works well as a thickener because of its low solubility. It provides an alkali reserve for the depilation processes to keep the pH high enough for hair or wool loosening. It is readily available, and best of all it is cheap. Lime is still used for paint thickening in quite a high proportion of fellmongeries. However lime does have disadvantages when used as a thickener. In general, it does not stay in suspension. Furthermore, pelts painted with a low lime-paint tend to have a brighter grain, and they require less washing out of lime and are easier to delime. A number of alternative thickeners have been tried. Among the most successful are pregelatinised potato starch ethers. Pregelatinised potato starch ethers give good thickening at low concentrations of 1.5 to 3 percent. They are reasonably easy to mix into the paint, at least compared to some of the alternative non-lime thickeners, and they do not require any heating. However, in general they are not as easy to mix as lime. Unlike some of the non-lime thickeners, they are not so tacky that they cause sticking problems, with pelts sticking to each other or the boards of the pulling machines. They do not tend to have drip problems, and paint thickened with these thickeners is stable when sprayed under pressure. With some thickeners thinning under pressure leads drip problems. By using some lime in the system to act as an alkali reserve, sodium hydroxide is not needed to increase the pH. However there have been some problems in production. Paints thickened with these thickeners not always have behaved completely consistently when sprayed onto pelts, and this has caused problems of too much or too little paint on the pelts, or uneven coverage. This can lead to difficult pulling or residual wool problems or in some cases pelt damage.

It is thought that these inconsistencies are due to small changes in the viscosity of the paint from day to day, due to slight changes in the proportion of ingredients or the method of mixing, or even the temperature during mixing or application of the paint. Small differences in viscosity could lead to differences in application rate because a spray system is very sensitive to viscosity changes.

The operation of the depilation process can be looked at in two ways;

a) The Processes Taking Place in the Fellmongery

These are the observable processes that are carried out in the fellmongery on the skin and are controlled by the fellmongery manager. The process-steps involved may consist of; Wash; pre-flesh; squeeze or spin dry; apply depilatory paint; hold skins; remove wool.

Each of these processes are controlled to give good clean hair or wool removal with minimal damage to the skin.

b) The Underlying Processes

This requires an understanding of what is occurring as the depilatory paint is penetrating the skin, i.e.

how do sulphide and hydroxide penetrate the skin;
how much hydroxide and sulphide bind to the collagen in the corium layer;
how the sulphide and hydroxide react with the wool roots;
the equilibrium between sulphide and hydrosulphide.

To date, depilation research has looked at the processes carried out on the skin and their improvement without looking at the underlying processes that are occuring in the skin. Approaching depilation from the view of the underlying processes will enable the critical processes to be determined. These processes can then be optimised to give better depilation performance.

The optimisation and control of these critical processes depend on the ability to observe what is occurring, both on the underlying processes and the processes carried out. Factors which are of importance during depilation are:

thickness of skin; paint performance; paint application rate; rate of penetration of chemicals.

Current techniques for application of depilatory paint involve applying a larger amount of depilatory paint to the centre of the skin. This is to compensate for the assumed 2:1 ratio between the thick and thin regions of the skin. However the actual ratio between the thick and thin regions of the skin may be much larger than assumed. This may mean that the differential spraying technique may not deliver enough paint to the thicker areas of the skin.

If the correct amount of paint at the correct concentration is applied to the skin, there may still be problems with depilation if the spray pattern does not hold. Common starch thickeners are currently used in the industry to hold the spray pattern. However, even with the addition of common starch thickeners it is often found that when the skins are stacked or pole hung that the spray pattern will shift. A correctly thickened paint should not produce such paint migration.

To ensure that paint migration does not occur, a depilatory paint must be thickened correctly with a suitable thickener. The means of determining the suitability of a thickener for depilatory paints has not always been well understood. Often the thickener used has relied on suggestions from chemical companies. The selection of a thickener by this means may not always meet-the requirements of depilation. To determine the suitability of a thickener for a depilatory paint, the requirements of depilatory thickeners must be understood. These requirements can be put into four categories:

1) Viscosity Requirements

For a thickener to be considered suitable, the thickener must provide the required level of viscosity consistently and simply. Special handling requirements limit the use of the thickener in the fellmongery situation. To satisfy this the thickener should;

Thicken at normal temperatures (20–25° C.) without requiring heating.

easily disperse without lumping into sulphide solutions without the need for high speed agitators.

not be sensitive to shear.

2) Stability Requirements

Not only should a depilatory thickener provide the required level of viscosity, but it should also be stable, ie the thickener should not be broken down or form solid gels by process or chemical conditions. This can be satisfied if the thickener;

is not thinned excessively by mixing too long.

is stable under high NaOH and sulphide concentrations, e.g. does not gel or thin over time.

provides paints of consistent viscosity, e.g. will make the same paint again and again.

3) Tack Requirements

When two skins are placed together flesh to flesh after depilatory has been applied, there maybe some adhesion of the skins making pulling apart difficult. To be acceptable as a depilatory paint thickener, the thickener should not adhere skins when skins are placed together flesh to flesh for 2–3 hours.

4) Downstream Processing Requirements

The use of the thickener should not have any adverse effects on any further processing that may be carried out. The thickener;

should not affect the quality of the slats produced.

should not affect the quality of the slipe wool produced.

should not increase the waste treatment loading.

should easily be washed out.

SUMMARY OF THE INVENTION

The invention provides a depilatory paint thickener comprising a starch containing essentially only amylopectin molecules. Such a thickener is among others easily soluble in cold water; improves diffusion of chemicals (like sulphide or lime) throughout the skin; improves viscosity or resistance to shear of a paint, whereby less starch is needed to exert a similar effect; and increases the suspendability of a lime, allowing less lime to be used which creates environmental advantages in waste disposal.

SUMMARY OF THE INVENTION

Starches, both of the common variety containing both amylose and amylopectin, obtained from both cereals and tubers or roots and of the waxy variety, containing essentially only amylopectin molecules (e.g. 0–5% amylose), obtained from cereals, are widely used in foodstuff.

Common starch consists of two major components, an, in essence, linear $\alpha(1–4)$D-glucan polymer (branching is found at a low level) and a elaborately branched $\alpha(1–4$ and $1–6)$D-glucan polymer, called amylose and amylopectin, respectively. Amylose has in solution a helical conformation with a molecular weight in the order of $10^4–10^5$, or higher. Amylopectin consists of short chains of $\alpha$-D-anhydroglucopyranose units primarily linked by (1–4) bonds with (1–6) branches and with a molecular weight of up to $10^7$, or higher.

Amylose/amylopectin ratios in native starches in plants are generally anywhere at 10–40 amylose/90–60% amylopectin, also—depending on the variety of plant studied. In a number of plant species mutants are known which deviate significantly from the above mentioned percentages. These mutants have long been known in maize (corn) and some other cereals. Waxy corn or waxy maize has been studied since the beginning of this century. Therefore, the term waxy starch has often been equated with amylose free starch, despite the fact that such starch was in general not known from other starch sources such as potato but mainly derived from corn. However, industrial use of an amylose free starch has never occurred in depilation processes in fellmongeries.

In a preferred embodiment of the invention a depilatory paint thickener is provided wherein said starch containing essentially only amylopectine molecules has been derived from a genetically modified plant. Amylose production in a plant is among others regulated by the enzyme granule-bound starch synthase (GBSS), which is involved in generating the amylose content of starch, and it has been found that many of the waxy cereal mutants described above lack this enzyme or its activity, thereby causing the exclusive amylopectin character of these apparently naturally genetically modified cereal mutants.

An example of a thickener provided by the invention is a starch obtained from an amylose-free potato plant which is for example lacking GBSS activity or GBSS protein altogether, thereby lacking amylose and having essentially only amylopectin molecules. In a preferred embodiment of the invention a depilatory paint thickener is provided wherein said starch from is derived from a genetically modified non-cereal plant, for example from a potato, banana, yam, canna or cassave. Genetic modification of non-ceraeal plants such as tuber or root plants is a skill available to the artisan, and for example involves modification, deletion of or insertion in or (antisense) reversion of (parts of) a gene, such as a gene encoding granule-bound starch synthase (GBSS), which is involved in determining the amylose content of starch. In order to manipulate such crop plants, efficient transformation systems and isolated genes are available, especially of potato, and others are found by analogy. Traits, such as absence of amylose, that are introduced in one variety of a crop plant can easily be introduced into another variety by cross-breeding. In the experimental part of this description a thickener is provided wherein said modified starch is obtained from a genetically modified potato, for example from a genetically modified potato plant variety. Examples of such a potato plant variety are the variety Apriori, Apropos or Aropect, or varieties derived thereof.

In a further embodiment of the invention a depilatory paint thickener is provided wherein said starch is a cross-linked starch, such as a epichlorohydrin cross-linked starch.

Crosslinking starch is in itself a method available to the artisan, various cross-linking agents are known, examples are epichlorohydrin, sodium trimetaphosphate, phosphorous oxychloride, chloroacetic acid, adipic anhydride, acrolein, dichloro acetic acid or other reagents with two or more anhydride, halogen, halohydrin, epoxide or glycidyl groups or combinations thereof which all can be used as crosslinking agents.

In a preferred embodiment a depilatory paint thickener is provided having a degree of cross-linking varying from 0.001% to 0.5%, preferably varying from 0.01% to 0.1%, more preferably varying from 0.025% to 0.05%, for example varying on whether the cross-linking occurs in solution or suspension. In the experimental part of this description a much preferred thickener is provided having a degree of cross-linking of between 0.025% to 0.05%, such as 0.033%, cross-linked in solution.

In yet another embodiment of the invention a depilatory paint thickener is provided wherein said starch is a stabilised starch, such as a hydroxyalkylated starch. Stabilisation by hydroxyalkylation or carboxymethylation of starch is for example obtained with reagents containing a halogen, halohydrin, epoxide or glycidyl group as reactive site. Chloro acetic acid (or its salt) is used as carboxymethylation reagent. In one embodiment of the invention said starch is stabilised by hydroxypropylation, hydroxybutylation, hydroxyethylation and/or carboxymethylation.

In a preferred embodiment of the invention a depilatory paint thickener is provided comprising a stabilised starch having a molar degree of substitution (MS) varying from 0.01 to 1.6, preferably from 0.1 to 1.2, more preferably from 0.2 to 0.8.

In a further embodiment, the invention provides a depilatory paint thickener wherein said starch is an pregelatinised or cold-water soluble or instant starch, providing easy solubility to a thickener. In general starch or starch derivatives are relatively insoluble in cold water. Viscosity and water binding is achieved by heating or cooking. For convenience starches are sometimes pre-gelatinised i.e. pre-cooked and dried. These starches are referred to as instant starches and perform without heating or cooking. Pre-gelatinisation can for example be achieved by spray cooking, spray drying, roll drying, drum drying, extrusion heating in aqueous water-miscible organic solvents or under high pressure.

A paint thickener as provided by the invention provides good and stable viscosity and shear resistance to a depilatory paint. Due to its high and stable viscosity and water binding properties, it can in general be used at lower concentrations than a thickener comprising a common starch with normal contents of amylose. It provides protection against abrasion of skins, especially during the stacking of the skins. It furthermore enables easier separation of stacked, limed pelts as it prevents drying out of the paint due to its high water binding properties.

The invention furthermore provides a depilatory paint comprising a thickener as provided by the invention. Such a depilatory paint can advantageously be used in a depilation process. Such a paint provides faster penetration of the paint chemicals through fat deposits, whereby it emulsifies the fat. In such a paint, the lime concentration or pH is easy to adjust, due to the stable viscosity of the product under various concentrations of chemicals used. In general, less lime is needed to exert a similar function and sulphide strength is increased.

The invention further more provides a method for depilating an animal hide or skin comprising treating said hide or skin with a depilatory paint provided with a depilatory paint thickener according to the invention. Such a method provides easier and effective pulling, contributing to an even and high quality of the produced slats and leather. The risk of abrasion is minimised, thereby reducing the number of damaged slats or pelts to go into the pickling and chrome tanning process, thereby reducing the number of pelts that turn out as damaged wet-blue after tanning.

The invention furthermore provides a depilated hide or skin produced by a method according to the invention and provides leather or a leather product derived thereof. Such hides or skin and leather and leather products are characterised by more even tanning and less abrasions, having a good clear grain and no mottle.

The invention further provides (slipe) wool obtained from a hide or skin treated by a method according to the invention. Such a wool is brighter and softer and less damaged than ordinary slipe wool, and finds better use.

The invention is further described in examples, tables and figures in the experimental part of the description which are not limiting the invention.

EXAMPLE 1

The main properties required for a thickener of depilatory paints are:

high thickening power in depilatory paints, stability on ageing, good reproducibility of the preparations, good stability to shear, easy dispersion of the flakes in the depilatory paints, no lump forming.

In example 1 the properties of 3 commercial products, based on potato starch, commonly used in the depilatory paints (products A, B and C) have been compared with 2 other products also based on potato starch (products O and P) and a product based on amylopectin potato starch (product I).

1Experiments
1.1Measurements of Brookfield Viscosity in Tap Water
Preparation of a solution by:

dispersion under mechanical stirring at 450 rpm (6 holes-blade stirrer) of the starch in tap water in order to have a total weight of 500 g;

stirring at 450 rpm for 30 minutes;

rest for 15 minutes;

measurement of the viscosity at 20° C. with a Brookfield viscometer RVT at 50, 20 and 10 rpm.

Measurements have been done at several concentrations for each product depending on their level of viscosity. With the products O and P, the addition of a few drops of an anti-foaming agent is necessary.

1.2Stability to Ageing

The stability to ageing has been evaluated by measuring the Brookfield viscosities of the previous preparations after 4 hours and 24 hours resting time.

1.3Stability with Lime

The viscosities of preparations containing 2% lime have been compared with the viscosities of the preparations without lime. 2 different methods have been used for the preparations with lime.

a) addition of lime before starch:

dispersion under mechanical stirring of 10 g lime in tap water in order to have a total weight with starch of 510 g;

stirring at 450 rpm (6 holes-blade stirrer) for 5 minutes;

dispersion at 450 rpm of the starch and stirring at 450 rpm for 30 minutes;

rest for 15 minutes;

measurement of the viscosity at 20° C. with a Brookfield viscometer RVT at 50, 20 and 10 rpm.

b) addition of lime after starch:

dispersion under mechanical stirring at 450 rpm (6 holes-blade stirrer) of the starch in tap water in order to have a total weight with lime of 510 g;

stirring at 450 rpm for 30 minutes;

dispersion at 450 rpm of 10 g lime and stirring for 1 minute at 450 rpm;

rest for 15 minutes;

measurement of the viscosity at 20° C. with a Brookfield viscometer RVT at 50, 20 and 10 rpm.

In the 2 methods, the viscosities have been measured again after 24 hours rest.

The tests with lime have been made on preparations having a Brookfield viscosity at 20° C., 20 rpm of about 5000 mPa.s ±500 mPa.s 1.4 Stability to Shear The viscosities of the preparations submitted to 30 minutes of intense shear at 1500 rpm have been compared to the viscosities of the same preparations before shear:

dispersion under mechanical stirring at 450 rpm (6 holes-blade stirrer) of the starch in tap water with a few drops of an anti-foaming agent in order to have a total weight of 500 g;

stirring at 450 rpm for 30 minutes;

rest for 15 minutes;

measurement of the viscosity at 20° C. with a Brookfield viscometer RVT at 50, 20 and 10 rpm;

stirring at 1500 rpm (6 holes-blade stirrer) for 30 minutes;

immediately after, measurement of the viscosity at 20° C. with a Brookfield viscometer RVT at 50, 20 and 10 rpm;

rest for 24 hours and measurement of the viscosity at 20° C. with a Brookfield viscometer RVT at 50, 20 and 10 rpm.

1.5 Viscosities in a Formulation of Depilatory Paint

Formulation:

tap water: 270 g lime (calcium hydroxide): 6 g sodium sulphide 35%: 72 g starch thickener: 4.5 or 6 g.

This corresponds to:

water: 100 g lime: 2 g sodium sulphide 60%: 14 g starch thickener: 1.5 or 2 g.

The following method has been used for the preparation and viscosity measurements:

dissolving of the sodium sulphide in the water;

dispersion of the lime under mechanical stirring and stirring for 5 minutes;

dispersion of the starch at 450 rpm (4 blades propeller) and stirring for 30 minutes;

rest for 15 minutes;

measurement of the viscosities at 20° C. with a Ford cup nr 4 and with a Brookfield viscometer RVT at 100, 50, 20 and 10 rpm.

2 Results and Discussion 2.1 Viscosities of Preparations in Tap Water

See Table 2.

A Brookfield viscosity at 20 rpm of about 5000 mPa.s±500 mpa-,s is obtained with:

product A at the concentration of 3.5%, product B at the concentration of 7.5%, product C at the concentration of 6.3%, product O at the concentration of 10.0%, product I at the concentration of 3.5%.

Product I based on amylopectin potato starch has a viscosity comparable with the product A at the concentration of 3.5%. The preparations of product I are fairly transparent and have a smooth and short texture, rather comparable with the preparations of product C. The speed of swelling for product I is a little bit slower than for product C, but is faster than for products A and B.

The products O and P have a comparable viscosity which is much lower than the viscosity of the 4 other products. They generate an important amount of foam in case of stirring without anti-foaming agent. Their preparations have also a texture different from the other products, much longer which indicates that their effective degree of crosslinking is lower than the degree of crosslinking of the other considered products.

2.2 Stability to Ageing

See table 3.

The preparations in tap water are perfectly stable during at least 24 hours for all the products.

2.3 Stability with Lime

In the range of tests with lime, preparations of the products A and I at 3.5%, product C at 6.3%, product O at 10%, which have without lime about the same viscosity, have been compared. The 4 compared starches exhibit with lime different behaviours (see—table 4).

For product I, the addition of lime causes an increase of the viscosity, probably due to better swelling in alkaline conditions. It is interesting to remark that the increase of viscosity is about the same whatever the addition of the lime is done before of after the addition of the starch. The viscosities obtained with lime are stable on ageing during at least 24 hours. This indicates that the viscosity of alkaline preparations is not dependent on the order of introduction of the reagents.

For product O, the increase of viscosity with lime is more important than for product I. The texture of the preparations has changed a lot by taking a highly rubbery character, especially after 24 hours ageing.

The product C is the only product for which a strong decrease of viscosity is observed with lime, probably due to its low hydroxypropyl MS, in comparison with the other products.

2.4 Stability to Shear

For the tests of stability to shear, again preparations of the products A and I at 3.5%, C at 6.3%, and O at 10% have been compared (see table 5).

The decrease of viscosity is more important for the products I and O (loss of about ½ of the initial viscosity) than for the products A and C (loss of about ⅓ of the initial viscosity). Most part of the initial viscosity is recovered after 24 hours rest. The resistance to shear of the 4 products can be judged satisfactory, considering the severity of the laboratory test. Under factory conditions, the shear stresses applied during the preparation and the storage of the depilatory paints are probably much lower.

2.5 Viscosities in the Formulation of Depilatory Paint

See table 6.

Product I has in the depilatory paint a much higher thickening power than all the other products, at the concentration of 2%, whatever the shear rate of the viscosity measurement. At the concentration of 1.5%, the viscosity curves of the products I and C are comparable, apart from the measurement at 10 rpm which is a little bit higher for product C.

The 2 other products O and P, which have a low viscosity in tap water, exhibit also a low viscosity in the depilatory paint.

3 Conclusion

The product I based on amylopectin potato starch has very good thickening properties in tap water as well as in depilatory paint. In addition to that, it is easy to prepare and dissolves rather quickly, has a good behaviour with lime, and has a satisfactory resistance to shear. Consequently such a product presents a great interest for an application in depilatory paints.

Certain characteristics of the product I are different from the products A and C. In comparison with the product A, the product I has:
 a much higher viscosity in depilatory paint, especially at the concentration of 2%,
 a higher speed of swelling,
 a better behaviour with lime.
In comparison with the product C, the product I has:
 a much higher viscosity in depilatory paint,
 a much higher viscosity in tap water and alkaline water,
 a better resistance to lime.

The B products B, O and P based on potato starch have a much lower thickening effect than the other products both in depilatory paint as in tap water.

EXAMPLE 2

The example I has shown that the product I based on amylopectin potato starch I has very good characteristics for an application as thickener in depilatory paints for fellmongeries.

The crosslinking of the product I has been realized in suspension. Example 2 relates to samples of a comparable type of amylopectin potato starch, but prepared according to the process of crosslinking in solution, and also to samples of a comparable type of starch based on waxy-maize starch and crosslinked in suspension.

9 samples have been tested which can be classified in 3 ranges of products:
 4 samples based on amylopectin potato starch with a hydroxypropyl MS of 0.6, crosslinked in solution with different amount of epichlorohydrin(ECH),
 3 samples based on amylopectin potato starch with a hydroxypropyl MS of 0.2, crosslinked in solution with different amount of epichlorohydrin,
 2 samples based on waxy-maize starch with a hydroxypropyl MS of 0.6, crosslinked in suspension with different amount of epichlorohydrin.

The viscosities of these 9 samples have been measured according to similar methods in the same formulation of depilatory paint. The results have been compared to the viscosities measured on the products I, A and C, previously discussed in example 1.

1 Experiments

The same procedures as in example 1 have been used concerning the measurements of viscosity in tap water and in the formulation of depilatory paint, the stability to ageing, with lime and to shear.

The speed of swelling of the different starches have been evaluated by recording, with a Haake viscometer RV 12, curves of viscosity as function of the time (dispersion of the flakes in water in about 2 seconds, time 0=end of the dispersion of the flakes in water, total time of record: 15 min). Samples have been added at the concentration of 4% (2.40 g sample for 60 g tap water), apart from for the low viscous products, i.e. the products B at 7% and C at 6%.

For trials with water alkalinized with lime, 1.20 g lime (2%) has been dispersed in water prior to the addition of the starch.

2 Results and Discussion
2.1 Viscosities of Preparations in Tap Water
See table 7.

All 9 samples have a much higher viscosity than product C. At the concentration of 5%, for the 3 ranges of samples, the viscosities are all higher when the degree of crosslinking is higher. It is the opposite at the concentration of 2%: the viscosities appear lower when the degree of crosslinking increases. This can be explained by an incomplete swelling of the product during the stirring time when the starch concentration is low, and the concentration of swollen material is all the lower as the degree of crosslinking increases.

For a same degree of crosslinking, the samples based on amylopectin potato starch with a hydroxypropyl MS of 0.6 have a higher viscosity than the samples based on amylopectin potato starch with a hydroxypropyl MS of 0.2. The 2 samples based on waxy-maize starch have also a lower viscosity than the samples based on amylopectin potato starch with the same hydroxypropyl MS of 0.6. A Brookfield viscosity at 20 rpm of about 500 mPa.s±500 mpa.s is obtained at the concentration of:
 3.3% for product E,
 3.5% for products A and I,
 3.6% for product G,
 4.0% for products K, J and M,
 5.0% for product D,
 6.3% for product C.

The viscosity curves as function of the concentration are comparable for the products E and I.

2.2—Stability to Ageing
See table 8.

In difference with product I, a slight loss of viscosity can be observed for most of the new samples after 24 hours storage. This loss is all the higher as the degree of crosslinking is lower, and is also higher for the products having a hydroxypropyl MS of 0.2 instead of 0.6. The difference of viscosity after 24 hours storage is not significant for the more crosslinked products based on amylopectin potato starch (products H, G and L), but is important for the less crosslinked products (products D and J).

2.3—Speed of Swelling
See table 9.

In tap water, the speed of swelling is higher for the products based on amylopectin potato starch having a hydroxypropyl MS of 0.6, than for:
 the products based on amylopectin potato starch having a hydroxypropyl MS of 0.2,
 the products based on waxy-maize,
 the product A based on potato starch.

The products with the highest degree of crosslinking in each range of samples have a lower speed of swelling. The products E and I give comparable curve of swelling.

Although its high degree of crosslinking, product B has a high speed of swelling if prepared at high concentration (7%).

With water containing 2% lime, the samples based on amylopectin potato starch having a hydroxypropyl MS of 0.6 have a higher viscosity than in tap water, especially those having the highest degree of crosslinking. The speeds of swelling are not very different from the speed of swelling in tap water. The products E and I give again comparable curve of swelling. For products based on amylopectin potato starch having a hydroxypropyl MS of 0.2, the end-viscosities are much lower than in tap water, and the speeds of swelling are still low.

The product A exhibits a very low speed of swelling in alkaline water. After 15 min stirring, its swelling is far to be complete.

The product C swells very fast, but the end-viscosity is much lower than in tap water. The low end-viscosity in water alkalinized with lime is a consequence of its low hydroxypropyl MS.

2.4 Viscosities in the Formulation of Depilatory Paint

See:
- tables 10 and 11 for viscosities of depilatory paints containing 2.0% starch,
- table 12 for viscosities of depilatory paints containing 1.5% starch.

For the range of samples based on amylopectin potato starch with MS 0.6, the highest viscosities are obtained for the product E having an intermediary degree of crosslinking (% ECH: 0.025). The more crosslinked product (product H—% ECH: 0.10) gives the lowest viscosities. The 2 other samples (product G—% ECH: 0.05 and product D—% ECH: 0.0125) have an intermediary thickening power. The curve of viscosity of the product E at the concentration of 2.0% is very close to the curve of the product I. At the concentration of 1.5%, the product E gives even higher viscosities than the product I.

For the range of samples based on amylopectin potato starch with MS 0.2, the viscosities are all the highest as the degree of crosslinking is lower. As for the previous range of amylopectin potato starch samples, the more viscous product has been produced with 0.025% ECH (product J). At the concentration of 2.0%, the products with MS 0.6 are more viscous than products with MS 0.2 for a same degree of crosslinking. At the concentration of 1.5%, the product J has a slightly lower viscosity than the product E when measured at a high shear rate (100 and 50 rpm), but is characterised by a higher viscosity when measured at a low shear rate (10 rpm). The best products of the range of samples based on amylopectin potato starch with MS 0.2 have a better thickening power than the products A, B and C based on potato starch.

The 2 waxy-maize based products have lower viscosities than the amylopectin potato starch based products. The product M, which is the less crosslinked, is the more viscous of these 2 products.

A decrease of viscosity is observed on the depilatory paints during storage, with certain samples based on amylopectin potato starch and MS 0.6, especially at the concentration of 2% and for measurements at low shear rate (10 and 20 rpm). This decrease is of the order of 10% for the measurements at 20 rpm, the most part occurs during the first 4 hours storage. This is not observed with the samples based on amylopectin potato starch and MS 0.2, for which a small increase of viscosity rather occurs. An explanation could be that for products with MS 0.6 and at the concentration of 2%, the first measurement after preparation corresponds to a state at/or near the peak of swelling. At a lower concentration, e.g. 1.5%, there is no peak during the swelling, and consequently the measurements of viscosity after preparation and after 4 hours are close. The products with MS 0.2 need a longer time for a complete swelling, and have no viscosity peak at the 2 considered concentrations (see also table 9).

On the whole, each of the 3 ranges of products, and especially the ranges of products based on amylopectin potato starch, contains products which enable to obtain high viscosities in depilatory paint. Its curve of viscosity at the concentration of 2.0% is very close to the curve of the product I. At the concentration of 1.5%, E gives even higher viscosities than I.

2.5 Stability with Lime

Certain samples (those which have given the best results in depilatory paints for each range of products) have been prepared with 2% lime at the following or concentration:

product E (amylopectin potato starch—MS 0.6): 3.3% product J (amylopectin potato starch—MS 0.2): 4.0% product M (waxy-maize starch—MS 0.6): 4.0%.

These concentrations enable to reach in tap water about the same level of viscosity (see table 13). The table 9 has also to be taken into account.

A different behaviour is observed between the samples with a MS of 0.6 and the products with a MS of 0.2.

The products with MS of 0.6 give in the presence of lime slightly increased viscosities, not very dependent of the order of introduction of the lime. Only the viscosities after 24 hours of storage when lime is added after the swelling of the starch are significantly higher.

For the product J, the swelling is strongly inhibited when lime is added before starch, and in any case the viscosity after 24 hours of storage are very low. This behaviour is also different from the behaviour of the product C, for which the viscosities are much lower with lime than in tap water.

It must also be noted that the behaviour of certain of the considered products in water with 2% lime is rather different to the behaviour in the depilatory paint which contains in addition sodium sulphide; e.g. the products C and J give very low viscosities in water with lime, but relatively high viscosities in the depilatory paint. The product E gives high viscosities in water with lime as well as in depilatory paints.

2.6 Stability to Shear

The tests of stability to shear have been done on the same samples and at the same concentration than tests with lime (see table 14).

As previously mentioned for product I, a higher decrease of viscosity is observed for the products E and J than for the products A and C. The product M based on waxy-maize starch has given intermediary results. The recovery of viscosity is low after 24 hours rest for the product J which has a low hydroxypropyl MS.

It must be recalled that this test is probably much more severe than the shear stresses applied during the preparation and the storage of the depilatory paints.

3 Conclusion

The products based on amylopectin potato starch, especially those having a hydroxypropyl MS of 0.6 such as the product E, have good thickening properties for the depilatory paints. The characteristics of the product E are very close to the characteristics of the product I.

The products based on amylopectin potato starch, especially the products E and I, have as main advantages in front of the products A and C based on potato starch, of a higher viscosity in depilatory paint and a lower sensitivity to lime. They have also in front of the product A the advantages of a much higher speed of swelling.

High visosities in depilatory paint can also be obtained with the products based on amylopectin potato starch with a MS of 0.2, such as the products J and K. The best products of this range of samples have a better thickening power than the products A and C based on common potato starch.

The samples based on waxy-maize starch have lower viscosities and a slightly lower speed of swelling than the best products based on amylopectin potato starch with a MS of 0.6. Their thickening power in depilatory paints is nevertheless comparable and in certain conditions higher than the products based on common potato starch.

EXAMPLE 3

Pregelatinized hydroxypropylated crosslinked starch based on amylopectin potato starch, especially the products E and G, have very good characteristics for an application as thickener in depilatory paints for fellmongeries.

Another sample (product F) based on amylopectin potato starch has been prepared according to the same process of production (crosslinking in solution) as the products E and G. The new sample has the same hydroxypropyl MS (0.6), but has an intermediary degree of crosslinking (0.033% epichlorohydrin instead of 0.025% for E and 0.050% for G).

The characteristics of the product F (viscosities in tap water and in a depilatory paint, speed of swelling, characteristics of stability) have been measured according to similar methods as in example 2 and compared to the characteristics of the products E and G.

1 Experiments

The test procedures are identical to the procedures described in example 2.

The measurements of viscosity in tap water and in the depilatory paint, and the stabilities to ageing have been made again on the products E and G, in order to check the repeatability of the results. The figures mentioned in the tables of this report are averages of the new results and the results previously indicated in example 2.

A test of swelling in water containing lime and sodium sulphide has been added to the tests of swelling in tap water and in water alkalinized with 2% lime, according to the same procedure (recorded with a Haake viscometer RV 12). The amounts of water (50.6 g), lime (1,2 g) and sodium sulphide 35% (14,4 g) have been calculated in order to have the same ratios than in the formulation of the depilatory paint, e.g.: 100% water–2% lime–14% sodium sulphide 60%. The amount of starch added is 2,4 g (4%). This percentage is much higher than in the depilatory paints, but is necessary for being in the range of viscosities which can be detected by the Haake viscometer. The order of introduction of the reagent is:

1. water
2. solubilization of the sodium sulphide;
3. dispersion of the lime, stirring during 2 minutes;
4. addition of the starch, start of the record of the swelling curve, (total time of record: 15 min).

2 Results and Discussion 2.1 Viscosities of Preparations in Tap Water
See table 15.

A Brookfield viscosity at 20° C. and 20 rpm of about 5000 mpa.s±500 mpa.s is obtained at the concentration of:

3.4% for product E,
3.5% for products F and A,
3.6% for product G.

The 3 products based on amylopectin potato starch and also the product A have about the same viscosity at the concentration of it 4.0%. Below 4.0%, the less crosslinked product (product E) has the highest viscosity and the more crosslinked product (product G) the lowest viscosity. It is the opposite at the concentration of 5.0%, the viscosity increases when the degree of crosslinking increases.

The new measurements of viscosity on the products E and G are not significantly different from the measurements mentioned in example 2.

2.2 Stability to Ageing
See table 16.

At very low concentration (2.0%), the viscosities after 24 hours rest are much higher than after preparation. To the difference of the preparations at higher concentration, not completely swollen particles can be observed in the preparations at 2%. The low concentrations, for which the viscosity reached after 30 minutes stirring is very low and not sufficient for suspending the not completely swollen material, need in fact a longer time of stirring.

At the intermediary concentrations (3.0–4.0%), a slight increase of the viscosity after 24 hours is generally observed.

At the concentration of 5.0%, there is a loss of viscosity after 24 hours rest which is all the lower as the degree of crosslinking is higher. For the 2 more crosslinked products (F and G), the difference of viscosity after 24 hours is very low.

2.3 Viscosities in the Formulation of Depilatory Saint
See table 17.

The product F has significantly the highest viscosity when added at the concentration of 1.5%, and is very close to the less crosslinked product (product E) at the concentration of 2.0%. These 2 samples are the most viscous products (with product I—see examples 1 and 2) in depilatory paint amongst all the considered products. The more crosslinked product (product G) has a lower thickening power than the 2 other samples based on amylopectin potato starch.

The decrease of viscosity during storage is in fact low for these 3 products. The new measurements of viscosity on samples E and G are not significantly different from the measurements mentioned in example 2.

2.4 Speed of Swelling
See table 18.

The speed of swelling in the 3 mediums (tap water, water alkalinized with 2% lime, water containing 2% lime and 14% sodium sulphide) of the 3 samples based on amylopectin potato starch have been compared to the curves of swelling of the products A, B and C.

The behaviours of these products are very different as function of the kind of water.

For the 3 samples based on amylopectin potato starch, the speed of swelling is close in tap water and in water alkalinized with lime, but the viscosity is higher with lime. The speed of swelling is a little bit higher in the presence of sodium sulphide. The highest speed of swelling with sodium sulphide is observed for F. The final viscosity is lower with sodium sulphide than with only lime for the less crosslinked product (product E), identical for the intermediary crosslinked product (product F), higher for the more crosslinked product (product G).

The property of for example product F to give very close viscosities in water containing only 2% lime and in water containing 2% lime+14% sodium sulphide is very interesting for an application in depilatory paints, because that means that the product will have the same behaviour whatever the percentage of sodium sulphide in the depilatory paint.

The product A needs a longer time for swelling than the 3 previous products, whatever the kind of water. The addition of 2% lime decreases the speed of swelling and the viscosity. The presence of the sodium sulphide in the alkaline water has a beneficial effect concerning the speed of swelling and the viscosity. But the final viscosity with lime and sodium sulphide is much lower than the 3 previous samples.

The product B has another type of behaviour. The speed of swelling is much faster in alkaline medium than in tap water, and viscosities are much higher. But the addition of sodium sulphide has an unfavourable effect on viscosity. The viscosities reached with the product B are much lower than with the 3 samples based on amylopectin potato starch.

The product C has also a behaviour different to all the other products. The swelling is very fast whatever the type of water. The presence of sodium sulphide provokes a strong increase of the viscosity in comparison with tap water or water with only lime.

2.5 Stability with Lime
See table 19.

For the 2 more crosslinked products (products F and G), the addition of lime provokes a significant increase of the viscosity. The increase of viscosity is about the same when the addition of lime is done before or after the starch. The obtained viscosities are stable to ageing during at least 24 hours. This indicates that for these 2 products, the viscosity of the alkaline preparation is not very dependent on the order of addition of the reagents.

For the less crosslinked product (product E), the increase of viscosity in the presence of lime is lower, especially when lime is added before starch. A significantly higher viscosity is observed after 24 hours storage when lime is added after the swelling of the starch. Consequently the viscosity in the presence of lime is for the product E more dependent on the order of addition of the reagents than the 2 previous products.

2.6 Stability to Shear
See table 20.

The decrease of viscosity is lower for the more crosslinked products (products F and G) than for the product E. The results of the test of shear are about the same for the products F and G. The resistance to shear of these products can be judged satisfactory considering the severity of the laboratory test.

3 Conclusion

The products based on amylopectin potato starch have good properties for an application in depilatory paints. They are characterised by:
- a high thickening power in depilatory paint, high viscosities can be obtained even at low concentration (1.5%), especially with the products E and F;
- a fast speed of swelling in the presence of lime and sodium sulphide;
- a viscosity not very dependent on the percentage of sodium sulphide, especially for the product F;
- a satisfactory stability to shear;
- a good stability to ageing.

These products can advantageously replace in this application the products based on common starch, such as product A due mainly to their higher viscosity in depilatory paint and their much higher speed of swelling, and such as product C which has a lower thickening effect in depilatory paint and a higher sensitivity to lime.

EXAMPLE 4

This example illustrates the use of a thickener of the present invention for the dehairing of hide or skin, according to a quick-pull system. In such a system, the pulling of the hairs from the skin can start no more than 2 hours after the paint has been sprayed on the skin. Typical depilation paints for quick-pull systems are characterized by the presence of sodium hydroxide and a high amount of sodium sulphide in their formulation.

The product A based on potato starch and the product F based on amylopectin potato starch have been tested in the following formulation:

water: 100 g
sodium hydroxide 2.3 g
lime (calcium hydroxide): 3 g
sodium sulphide 60%: 35 g
starch thickener: 2.2 g for A and 1.5 g for F.

The viscosities obtained with the products A and F after preparation are indicated in table 21. As already seen in the example 3, the product F has a higher thickening power than the product A. The same viscosity can be obtained at the concentration of 1.5% for the product F and at the concentration of 2.2% for the product A. The stability of the viscosity during time of the depilation paint with the product F is satisfactory. Only a small increase of viscosity is noted: from an initial viscosity of 270 mpa.s (at 20 rpm), the viscosity increase to 302 mPa.s after 4 hours storage and to 320 mPa.s after 24 hours storage.

EXAMPLE 5

This example illustrates the use of a thickener of the present invention for the dehairing of hide or skin, according to a long-pull system. In long-pull systems, the paint has a more gentle action of dehairing than in quick-pull systems, which decreases the risks of damage of the skins. Consequently the time of action of the paint must be longer (e.g. 5 hours) before starting the pulling of the hairs from the skin. Generally sodium hydroxide is not used in the formulation of the paints for long-pull systems.

Different products based on potato starch, amylopectin potato starch, and waxy-maize starch have been tested in the following formulation:

tap water: 100 g
lime (calcium hydroxide): 4 g
sodium sulphide 60%: 14 g
starch thickener: 1.5 g or 2.0 g.

For an easy dehairing, it is important to have a good migration of the paint through the skin, the paint being sprayed on what was the flesh side of the skin. This characteristic has been appraised by the help of a test of migration. The principle of the test is to measure the weight of paint which has been absorbed by a filter-paper after migration through a piece of leather during a given time. the procedure of the test is the following:
- sticking of a disc of leather on a metallic ring;
- placing of the ring on a weighed standardized paper-filter (disc of leather in contact with the paper-filter);
- pouring in the ring of 30 g depilation paint prepared according to the previous formulation;
- weighing of the paper-filter after a time of contact with the disc of leather of 15–30 and 60 minutes;
- calculation of the weight of liquid absorbed by the paper-filter after 15–30 and 60 minutes.

The speed of migration through the disc of leather is all the faster as the weight of liquid absorbed by the paper-filter after 15 minutes is higher.

The viscosities and the weight of liquid absorbed by the paper-filter are indicated for the different products tested according this formulation, in table 22.

A much higher viscosity can be reached with the products based on amylopectin potato starch, than with the other types of starch. The products H—L and Q, all based onamylopectin potato starch, have at the concentration of 1.5% a viscosity equal or higher to the viscosity at the concentration at 2.0% of the more viscous product of the samples based on potato starch (product C).

Certain products based on amylopectin potato starch combine a high thickening power with a high speed of migration through a leather skin. This is especially the case of the product Q, which despite the high viscosity of its preparation at the concentration of 1.5%, enables to prepare a depilation paint with a high speed of migration, comparable with the speed of migration measured on preparations (at the concentration of 2.0%) of the best samples based on potato starch.

TABLE 1

List of the products considered in the examples

| Product | Starch | Crosslinking[a] | ECH % | Hydroxy-propylation[a] | MS (HP) |
|---|---|---|---|---|---|
| A | PS | solution | 0.02 | solution | 0.7 |
| B | PS | suspension | 0.08 | solution | 0.8 |
| C | PS | suspension | 0.025 | suspension | 0.14 |
| D | APS | solution | 0.0125 | solution | 0.6 |
| E | APS | solution | 0.025 | solution | 0.6 |
| F | APS | solution | 0.033 | solution | 0.6 |
| G | APS | solution | 0.050 | solution | 0.6 |
| H | APS | solution | 0.100 | solution | 0.6 |
| I | APS | suspension | 0.010 | solution | 0.6 |
| J | APS | solution | 0.025 | solution | 0.2 |
| K | APS | solution | 0.033 | solution | 0.2 |
| L | APS | solution | 0.050 | solution | 0.2 |
| M | WMS | suspension | 0.02 | solution | 0.6 |
| N | WMS | suspension | 0.03 | solution | 0.6 |
| O | PS | solution | 0.0188 | solution | 0.66 |
| P | PS | solution | 0.0188 | solution | 0.75 |
| Q | APS | solution | 0.192 | solution | 0.2 |

[a]Method of derivatizing
PS = potato starch
APS = amylopectin potato starch
WMS = waxy maize starch

TABLE 2

Brookfield vicosities (mPa.s) at 20° C. of preparations in tap water as function of the concentration.

| | Concentration | | | | | | | | | | |
|---|---|---|---|---|---|---|---|---|---|---|---|
| | 2.0% | 3.0% | 3.5% | 4.0% | 5.0% | 6.0% | 6.3% | 7.0% | 7.5% | 8.0% | 10.0% |
| Product A | | | | | | | | | | | |
| 10 rpm | 470 | 3040 | 6960 | 15880 | 37200 | | | | | | |
| 20 rpm | 390 | 2320 | 4670 | 10320 | 23250 | | | | | | |
| 50 rpm | 290 | 1470 | 3000 | 5640 | 12300 | | | | | | |
| Product B | | | | | | | | | | | |
| 10 rpm | | | | | 80 | | | 3140 | 5880 | 13000 | 42000 |
| 20 rpm | | | | | 83 | | | 2550 | 4600 | 9450 | 26000 |
| 50 rpm | | | | | 84 | | | 1750 | 3050 | 5740 | 14120 |
| Product C | | | | | | | | | | | |
| 10 rpm | 24 | | | | 2960 | 5200 | 7520 | 21100 | 30000 | | |
| 20 rpm | 10 | | | | 2200 | 3730 | 5260 | 14100 | 20500 | | |
| 50 rpm | 18 | | | | 1480 | 2430 | 3360 | 8520 | 11900 | | |
| Product O | | | | | | | | | | | |
| 10 rpm | | 1220 | 11860 | | 2820 | 41000 | | 4200 | | 6280 | |
| 20 rpm | | 920 | 8870 | | 2120 | 25750 | | 3100 | | 4740 | |
| 50 rpm | | 640 | 4680 | | 1440 | 14420 | | 2100 | | 3220 | |
| Product P | | | | | | | | | | | |
| 10 rpm | | | | | 1130 | | | | | | |
| 20 rpm | | | | | 870 | | | | | | |
| 50 rpm | | | | | 610 | | | | | | |

TABLE 2-continued

Brookfield vicosities (mPa.s) at 20° C. of preparations in tap water as function of the concentration.

| | Concentration | | | | | | | | | |
|---|---|---|---|---|---|---|---|---|---|---|
| | 2.0% | 3.0% | 3.5% | 4.0% | 5.0% | 6.0% | 6.3% | 7.0% | 7.5% | 8.0% | 10.0% |
| Product I | | | | | | | | | | |
| 10 rpm | 260 | | 7920 | 11200 | 16500 | | | | | | |
| 20 rpm | 200 | | 5060 | 7160 | 10650 | | | | | | |
| 50 rpm | 134 | | 2860 | 4020 | 6050 | | | | | | |

TABLE 3

Stability to ageing of the preparations in tap water -
Brookfield viscosities (mPa · s) at 20° C.

| Product | A | B | C | O | I |
|---|---|---|---|---|---|
| Concentration | 3.5% | 10.0% | 6.3% | 10.0% | 3.5% |
| Viscosity after: | | | | | |
| preparation | | | | | |
| 10 rpm | 6960 | 42000 | 7520 | 6280 | 7920 |
| 20 rpm | 4670 | 26000 | 5260 | 4740 | 5060 |
| 50 rpm | 3000 | 14120 | 3360 | 3220 | 2860 |
| 24 hours | | | | | |
| 10 rpm | 7060 | 58000 | 7820 | 5650 | 7960 |
| 20 rpm | 4620 | 37600 | 5440 | 4340 | 5080 |
| 50 rpm | 2980 | 19800 | 3420 | 2930 | 2860 |

TABLE 4

Effect of lime on the Brookfield viscosities (mPa · s) at 20° C.

| Product | A | C | O | I |
|---|---|---|---|---|
| Concentration | 3.5% | 6.3% | 10.0% | 3.5% |
| Viscosity | | | | |
| without lime | | | | |
| 10 rpm | 6960 | 7520 | 6280 | 7920 |
| 20 rpm | 4670 | 5260 | 4740 | 5060 |
| 50 rpm | 3000 | 3360 | 3220 | 2860 |
| with 2% lime added before starch, measurement after preparation | | | | |
| 10 rpm | 3260 | 1430 | 17300 | 18700 |
| 20 rpm | 2080 | 1010 | 11650 | 11000 |
| 50 rpm | 1150 | 670 | 7140 | 5700 |
| measurement after 24 hours | | | | |
| 10 rpm | 4400 | 2420 | 20500 | 17000 |
| 20 rpm | 2880 | 1720 | 13500 | 9880 |
| 50 rpm | 1640 | 990 | 8200 | 4880 |
| with 2% lime added after starch, measurement after preparation | | | | |
| 10 rpm | 12600 | 760 | 22500 | 14200 |
| 20 rpm | 8460 | 550 | 14650 | 8600 |
| 50 rpm | 5130 | 327 | 8520 | 4420 |
| measurement after 24 hours | | | | |
| 10 rpm | 10520 | 880 | 30500 | 15000 |
| 20 rpm | 7240 | 616 | 19350 | 8620 |
| 50 rpm | 4900 | 362 | 11200 | 4260 |

TABLE 5

Effect of shear on the Brookfield viscosities (mPa · s) at 20° C.

| Product | A | C | O | I |
|---|---|---|---|---|
| Concentration | 3.5% | 6.3% | 10.0% | 3.5% |
| Viscosity after: | | | | |
| preparation | | | | |
| 10 rpm | 6960 | 7520 | 6280 | 7920 |
| 20 rpm | 4670 | 5260 | 4740 | 5060 |
| 50 rpm | 3000 | 3360 | 3220 | 2860 |
| 30 mn shear at 1500 rpm | | | | |
| 10 rpm | 4620 | 4940 | 3360 | 3700 |
| 20 rpm | 3450 | 3550 | 2580 | 2460 |
| 50 rpm | 2220 | 2320 | 1800 | 1500 |
| after 30 mn shear and 24 h rest | | | | |
| 10 rpm | 6900 | 5920 | 4680 | 6500 |
| 20 rpm | 4640 | 4230 | 3680 | 4120 |
| 50 rpm | 3040 | 2720 | 2560 | 2400 |
| Ratio: vis. after shear/ initial viscosity | | | | |
| 10 rpm | 0.66 | 0.66 | 0.54 | 0.47 |
| 20 rpm | 0.74 | 0.67 | 0.55 | 0.49 |
| 50 rpm | 0.74 | 0.69 | 0.58 | 0.52 |
| Ratio: vis. after shear and rest/ initial viscosity | | | | |
| 10 rpm | 0.99 | 0.79 | 0.75 | 0.82 |
| 20 rpm | 0.99 | 0.80 | 0.78 | 0.82 |
| 50 rpm | 1.01 | 0.81 | 0.80 | 0.84 |

TABLE 6

Ford cup 4 and Brookfield viscosities (mPa.s) of depilation paints (20° C.).

| | Product | | | | | | | | |
|---|---|---|---|---|---|---|---|---|---|
| | A | | B | C | | O | P | I | |
| | Concentration | | | | | | | | |
| | 1.5% | 2.0% | 2.4% | 1.5% | 2.0% | 2.0% | 2.0% | 1.5% | 2.0% |
| | pH | | | | | | | | |
| | 12.9 | 12.9 | 12.9 | 12.9 | 12.9 | 12.9 | 12.9 | 12.9 | 12.9 |
| Measurements after preparation | | | | | | | | | |
| Ford cup 4 (s) | 11.6 | 13.3 | 11.9 | 11.7 | 13.1 | 15.0 | 14.7 | 11.8 | 19.0 |
| Brookfield | | | | | | | | | |
| 10 rpm | 99 | 308 | 284 | 190 | 390 | 177 | 143 | 160 | 828 |
| 20 rpm | 75 | 197 | 157 | 116 | 234 | 145 | 123 | 107 | 580 |
| 50 rpm | 60 | 117 | 70 | 67 | 125 | 123 | 105 | 73 | 364 |
| 100 rpm | 51 | 93 | 55 | 58 | 92 | 112 | 98 | 67 | 258 |
| Measurements after 4 hours | | | | | | | | | |
| Ford cup 4 (s) | 11.6 | 13.3 | 11.2 | 11.7 | 13.1 | 14.7 | 14.3 | 11.6 | 18.3 |
| Brookfield | | | | | | | | | |
| 10 rpm | 92 | 304 | 77 | 190 | 367 | 145 | 144 | 147 | 812 |
| 20 rpm | 70 | 195 | 58 | 118 | 227 | 122 | 122 | 99 | 560 |
| 50 rpm | 58 | 117 | 46 | 68 | 127 | 103 | 104 | 69 | 348 |
| 100 rpm | 51 | 93 | 41 | 55 | 93 | 100 | 100 | 64 | 250 |
| Measurements after 24 hours | | | | | | | | | |
| Ford cup 4 (s) | 11.7 | 13.4 | 11.1 | 11.7 | 13.4 | 14.7 | 14.2 | 11.6 | 19.0 |
| Brookfield | | | | | | | | | |
| 10 rpm | 95 | 308 | 67 | 193 | 384 | 133 | 140 | 145 | 800 |
| 20 rpm | 73 | 202 | 54 | 120 | 250 | 113 | 118 | 100 | 558 |
| 50 rpm | 60 | 122 | 44 | 69 | 140 | 97 | 101 | 70 | 352 |
| 100 rpm | 51 | 94 | 39 | 57 | 108 | 93 | 97 | 64 | 252 |

TABLE 7

Brookfield vicosities (mPa.s) at 20° C. of preparations in tap water as function of the concentration.

| | Concentration | | | | | | | | |
|---|---|---|---|---|---|---|---|---|---|
| | 2.0% | 3.0% | 3.3% | 3.5% | 3.6% | 4.0% | 5.0% | 6.0% | 6.3% |
| Product A | | | | | | | | | |
| PS 10 rpm | 470 | 3040 | | 6960 | | 15880 | 37200 | | |
| MS 0.7 20 rpm | 390 | 2320 | | 4670 | | 6960 | 23250 | | |
| 50 rpm | 290 | 1470 | | 3000 | | 4670 | 12300 | | |
| Product I | | | | | | | | | |
| APS 10 rpm | 260 | | | 7920 | | 11200 | 16500 | | |
| MS 0.6 20 rpm | 200 | | | 5060 | | 7160 | 10650 | | |
| 50 rpm | 134 | | | 2860 | | 4020 | 6050 | | |
| Product H | | | | | | | | | |
| APS 10 rpm | | | | | | | 25800 | | |
| MS 0.6 20 rpm | | | | | | | 16100 | | |
| 50 rpm | | | | | | | 8720 | | |
| Product G | | | | | | | | | |
| APS 10 rpm | 138 | 2610 | | 6400 | 7920 | | 25000 | | |
| MS 0.6 20 rpm | 114 | 1705 | | 4160 | 5120 | | 15550 | | |
| 50 rpm | 89 | 1050 | | 2360 | 2880 | | 8400 | | |

TABLE 7-continued

Brookfield vicosities (mPa.s) at 20° C. of preparations in tap water as function of the concentration.

| | Concentration | | | | | | | | |
|---|---|---|---|---|---|---|---|---|---|
| | 2.0% | 3.0% | 3.3% | 3.5% | 3.6% | 4.0% | 5.0% | 6.0% | 6.3% |
| Product E | | | | | | | | | |
| APS 10 rpm | 312 | | 7080 | 9400 | | | 15800 | | |
| MS 0.6 20 rpm | 220 | | 4560 | 6000 | | | 10500 | | |
| 50 rpm | 148 | | 2550 | 3360 | | | 5620 | | |
| Product D | | | | | | | | | |
| APS 10 rpm | 640 | | | | | | 8000 | | |
| MS 0.6 20 rpm | 430 | | | | | | 5360 | | |
| 50 rpm | 258 | | | | | | 3220 | | |
| Product L | | | | | | | | | |
| APS 10 rpm | | | | | | | 18000 | | |
| MS 0.2 20 rpm | | | | | | | 11400 | | |
| 50 rpm | | | | | | | 6260 | | |
| Product K | | | | | | | | | |
| APS 10 rpm | 156 | | | | | 7820 | 13880 | | |
| MS 0.2 20 rpm | 120 | | | | | 4990 | 8840 | | |
| 50 rpm | 84 | | | | | 2820 | 4980 | | |
| Product J | | | | | | | | | |
| APS 10 rpm | 191 | | | 4500 | | 7840 | 12960 | | |
| MS 0.2 20 rpm | 137 | | | 2870 | | 5000 | 8360 | | |
| 50 rpm | 97 | | | 1650 | | 2840 | 4740 | | |
| Product N | | | | | | | | | |
| WMS 10 rpm | | | | | | | 13760 | | |
| MS 0.6 20 rpm | | | | | | | 8580 | | |
| 50 rpm | | | | | | | 4740 | | |
| Product M | | | | | | | | | |
| WMS 10 rpm | 125 | | | | | 7240 | 12400 | | |
| MS 0.6 20 rpm | 109 | | | | | 4600 | 7820 | | |
| 50 rpm | 79 | | | | | 2580 | 4340 | | |

TABLE 8

Stability to ageing of the preparations in tap water - Brookfield viscosities at 20°C. and 20 rpm.

| Product | Base | Hydroxy propyl MS | % ECH | Concentration (%) | Viscosity after preparation (mPa.s) | Viscosity after 24 hours ageing (mPa.s) |
|---|---|---|---|---|---|---|
| A | PS | 0.7 | 0.02 | 3.5 | 4670 | 4620 |
| I | APS | 0.6 | 0.01 | 3.5 | 5060 | 5080 |
| H | APS | 0.6 | o.1 | 5.o | 16100 | 15800 |
| F | APS | 0.6 | 0.05 | 3.6 | 5120 | 4940 |
| E | APS | 0.6 | 0.025 | 3.3 | 4560 | 4100 |
| D | APS | 0.6 | 0.0125 | 5.0 | 5360 | 2920 |
| L | APS | 0.2 | 0.05 | 5.0 | 11400 | 10520 |
| K | APS | 0.2 | 0.033 | 4.0 | 4990 | 3850 |
| J | APS | 0.2 | 0.025 | 4.0 | 5000 | 3110 |
| N | WMS | 0.6 | 0.03 | 5.0 | B5BO | 7500 |
| M | WMS | 0.6 | 0.02 | 4.0 | 4600 | 4870 |

TABLE 9

Swelling in tap water and in water alkalinized with 2% lime.

| Product | Base | Hydroxy propyl MS | % ECH | Medium and concentration | Peak time | Swelling Peak viscosity | Viscosity after 15 min |
|---|---|---|---|---|---|---|---|
| A | PS | 0.7 | 0.02 | TW 4% | ≧15' | — | 142 |
| | | | | AW 4% | ≧15' | — | 42 |
| B | PS | 0.8 | 0.08 | TW 7% | ≧15' | — | 71 |
| | | | | AW 7% | nm | nm | nm |
| | | | | AW 4% | 0'45" | 30 | 19 |
| C | PS | 0.14 | 0.025 | TW 6% | 4' | 89 | 82 |
| | | | | AW 6% | 1'55" | 42 | 29 |
| I | APS | 0.6 | 0.010 | TW 4% | 4'15" | 129 | 97 |
| | | | | AW 4% | 4'50" | 172 | 131 |
| H | APS | 0.6 | 0.100 | TW 4% | 8' | 61 | 60 |
| | | | | AW 4% | 7'30" | 135 | 127 |
| G | APS | 0.6 | 0.050 | TW 4% | 4'25" | 108 | 93 |
| | | | | AW 4% | 4'30" | 160 | 136 |
| E | APS | 0.6 | 0.025 | TW 4% | 4'45" | 136 | 92 |
| | | | | AW 4% | 5'00" | 160 | 115 |
| D | APS | 0.6 | 0.0125 | TW 4% | 3'35" | 141 | 76 |
| | | | | AW 4% | 3'45" | 123 | 86 |
| L | APS | 0.2 | 0.050 | TW 4% | 15' | 51 | 51 |
| | | | | AW 4% | 10' | 25 | 24 |
| K | APS | 0.2 | 0.033 | TW 4% | 8' | 79 | 72 |
| | | | | AW 4% | 12' | 27 | 26 |

TABLE 9-continued

Swelling in tap water and in water alkalinized with 2% lime.

| Product | Base | Hydroxy propyl MS | % ECH | Medium and concentration | Peak time | Peak viscosity | Viscosity after 15 min |
|---|---|---|---|---|---|---|---|
| J | APS | 0.2 | 0.025 | TW 4% | 10'50" | 78 | 74 |
|   |   |   |   | AW 4% | 14' | 45 | 44 |
| N | WMS | 0.6 | 0.03 | TW 4% | 15' | 45 | 44 |
|   |   |   |   | AW 4% | 6' | 86 | 78 |
| M | WMS | 0.6 | 0.02 | TW 4% | 9' | 62 | 58 |
|   |   |   |   | AW 4% | 6'10 | 96 | 82 |

TW = tap water
AW = water alkalinized with 2% lime
nm = not measurable

TABLE 10

Ford cup 4 and Brookfield viscosities of depilation paints (mPa.s) at 20° C. containing 2.0% starch, for amylopectin potato starch based products with a hydroxyropyl MS of 0.6

| Characteristics | Product | | | | | | |
|---|---|---|---|---|---|---|---|
|   | A | C | I | H | G | E | D |
| base | PS | PS | APS | APS | APS | APS | APS |
| MS | 0.7 | 0.14 | 0.6 | 0.6 | 0.6 | 0.6 | 0.6 |
| % ECH | 0.02 | 0.025 | 0.010 | 0.1 | 0.05 | 0.025 | 0.0125 |
| Measurements after preparation | | | | | | | |
| Ford cup 4 (s) | 13.3 | 13.1 | 19.0 | 14.8 | 16.1 | 20.2 | 18.8 |
| Brookfield | | | | | | | |
| 10 rpm | 308 | 390 | 828 | 392 | 448 | 720 | 508 |
| 20 rpm | 197 | 234 | 580 | 268 | 315 | 514 | 372 |
| 50 rpm | 117 | 125 | 364 | 170 | 205 | 334 | 254 |
| 100 rpm | 93 | 92 | 258 | 132 | 160 | 246 | 197 |
| Measurements after 4 hours | | | | | | | |
| Ford cup 4 (s) | 13.3 | 13.1 | 18.3 | 14.5 | 15.9 | 20.5 | 18.5 |
| Brookfield | | | | | | | |
| 10 rpm | 304 | 367 | 812 | 348 | 374 | 650 | 475 |
| 20 rpm | 195 | 227 | 560 | 240 | 284 | 478 | 356 |
| 50 rpm | 117 | 127 | 348 | 168 | 197 | 320 | 248 |
| 100 rpm | 93 | 93 | 250 | 130 | 156 | 240 | 194 |
| Measurements after 24 hours | | | | | | | |
| Ford cup 4 (s) | 13.4 | 13.4 | 19.0 | 14.9 | 15.9 | 20.2 | 18.0 |
| Brookfield | | | | | | | |
| 10 rpm | 308 | 384 | 800 | 326 | 362 | 630 | 440 |
| 20 rpm | 202 | 250 | 558 | 236 | 276 | 472 | 336 |
| 50 rpm | 122 | 140 | 352 | 164 | 196 | 320 | 236 |
| 100 rpm | 94 | 108 | 252 | 128 | 157 | 236 | 186 |

TABLE 11

Ford cup 4 and Brookfield viscosities of depilation paints (mPa.s) at 20° C. containing 2.0% starch, for amylopectin potato starch based products with a hydroxypropyl MS of 0.2, and for waxy-maize starch based products with a hydroxypropyl MS of 0.6.

| Characteristics | Product | | | | | | | |
|---|---|---|---|---|---|---|---|---|
|   | A | C | I | L | K | J | N | M |
| base | PS | PS | APS | APS | APS | APS | WMS | WMS |
| MS | 0.7 | 0.14 | 0.6 | 0.2 | 0.2 | 0.2 | 0.6 | 0.6 |
| % ECH | 0.02 | 0.025 | 0.010 | 0.05 | 0.033 | 0.025 | 0.03 | 0.02 |
| Measurements after | | | | | | | | |

TABLE 11-continued

Ford cup 4 and Brookfield viscosities of depilation paints (mPa.s) at 20° C. containing 2.0% starch, for amylopectin potato starch based products with a hydroxypropyl MS of 0.2, and for waxy-maize starch based products with a hydroxypropyl MS of 0.6.

| | Product | | | | | | | |
|---|---|---|---|---|---|---|---|---|
| | A | C | I | L | K | J | N | M |
| preparation | | | | | | | | |
| Ford cup 4 (s) | 13.3 | 13.1 | 19.0 | 14.9 | 15.7 | 16.1 | 14.2 | 15.2 |
| Brookfield | | | | | | | | |
| 10 rpm | 308 | 390 | 828 | 280 | 324 | 396 | 172 | 260 |
| 20 rpm | 197 | 234 | 580 | 204 | 248 | 290 | 140 | 198 |
| 50 rpm | 117 | 125 | 364 | 144 | 178 | 198 | 119 | 146 |
| 100 rpm | 93 | 92 | 258 | 121 | 145 | 154 | 106 | 126 |
| Measurements after 4 hours | | | | | | | | |
| Ford cup 4 (s) | 13.3 | 13.1 | 18.3 | 14.6 | 15.7 | 16.1 | 13.8 | 14.7 |
| Brookfield | | | | | | | | |
| 10 rpm | 304 | 367 | 812 | 320 | 332 | 432 | 172 | 228 |
| 20 rpm | 195 | 227 | 560 | 224 | 250 | 310 | 140 | 176 |
| 50 rpm | 117 | 127 | 348 | 148 | 178 | 203 | 116 | 136 |
| 100 rpm | 93 | 93 | 250 | 121 | 144 | 159 | 104 | 120 |
| Measurements after 24 hours | | | | | | | | |
| Ford cup 4 (s) | 13.4 | 13.4 | 19.0 | 14.8 | 15.7 | 16.1 | 13.8 | 14.9 |
| Brookfield | | | | | | | | |
| 10 rpm | 308 | 384 | 800 | 320 | 324 | 404 | 160 | 232 |
| 20 rpm | 202 | 250 | 558 | 224 | 244 | 300 | 124 | 180 |
| 50 rpm | 122 | 140 | 352 | 153 | 174 | 201 | 114 | 138 |
| 100 rpm | 94 | 108 | 252 | 124 | 143 | 158 | 105 | 121 |

TABLE 12

Ford cup 4 and Brookfield Viscosities of depilation paints (mPa.s) at 20° C. containing 1.5% starch.

| | Product | | | | | | | | |
|---|---|---|---|---|---|---|---|---|---|
| | A | C | I | G | E | D | K | J | M |
| Characteristics | | | | | | | | | |
| base | PS | PS | APS | APS | APS | APS | APS | APS | WMS |
| MS | 0.7 | 0.14 | 0.6 | 0.6 | 0.6 | 0.6 | 0.2 | 0.2 | 0.6 |
| % ECH | 0.02 | 0.025 | 0.01 | 0.05 | 0.025 | 0.0125 | 0.033 | 0.025 | 0.02 |
| Measurements after preparation | | | | | | | | | |
| Ford cup 4 (s) | 11.6 | 11.7 | 11.8 | 12.8 | 13.2 | 13.2 | 12.5 | 12.5 | 12.0 |
| Brookfield | | | | | | | | | |
| 10 rpm | 99 | 190 | 160 | 174 | 218 | 145 | 123 | 245 | 118 |
| 20 rpm | 75 | 116 | 107 | 125 | 158 | 119 | 92 | 152 | 86 |
| 50 rpm | 60 | 67 | 73 | 86 | 112 | 96 | 76 | 101 | 68 |
| 100 rpm | 51 | 58 | 67 | 81 | 100 | 89 | 73 | 88 | 63 |
| Measurements after 4 hours | | | | | | | | | |
| Ford cup 4 (s) | 11.6 | 11.7 | 11.6 | 12.6 | 13.2 | 13.2 | 12.5 | 12.5 | 12.0 |
| Brookfield | | | | | | | | | |
| 10 rpm | 92 | 190 | 147 | 152 | 196 | 153 | 130 | 240 | 116 |
| 20 rpm | 70 | 118 | 99 | 112 | 144 | 125 | 100 | 152 | 85 |
| 50 rpm | 58 | 68 | 69 | 82 | 105 | 99 | 78 | 97 | 67 |
| 100 rpm | 51 | 55 | 64 | 78 | 95 | 92 | 73 | 84 | 63 |
| Measurements | | | | | | | | | |

TABLE 12-continued

Ford cup 4 and Brookfield Viscosities of depilation paints (mPa.s) at 20° C. containing 1.5% starch.

| | Product | | | | | | | | |
|---|---|---|---|---|---|---|---|---|---|
| | A | C | I | G | E | D | K | J | M |
| after 24 hours | | | | | | | | | |
| Ford cup 4 (s) | 11.7 | 11.7 | 11.6 | 12.6 | 13.2 | 13.2 | 12.7 | 12.6 | 12.0 |
| Brookfield | | | | | | | | | |
| 10 rpm | 95 | 193 | 145 | 144 | 202 | 152 | 132 | 244 | 115 |
| 20 rpm | 73 | 120 | 100 | 109 | 154 | 122 | 98 | 161 | 85 |
| 50 rpm | 60 | 69 | 70 | 81 | 117 | 98 | 77 | 110 | 68 |
| 100 rpm | 51 | 57 | 64 | 77 | 103 | 90 | 72 | 96 | 64 |

TABLE 13

Effect of lime on the Brookfield viscosities (mPa.s) at 20° C. and 20 rpm.

| | Product | | | | | |
|---|---|---|---|---|---|---|
| | A | C | I | E | J | M |
| Characteristics | | | | | | |
| base | PS | PS | APS | APS | APS | WMS |
| MS | 0.7 | 0.14 | 0.6 | 0.6 | 0.2 | 0.6 |
| % ECH | 0.02 | 0.025 | 0.010 | 0.025 | 0.025 | 0.02 |
| Concentration | 3.5% | 6.3% | 3.5% | 3.3% | 4.0% | 4.0% |
| Viscosity without lime | 4670 | 5260 | 5060 | 4560 | 5000 | 4600 |
| Viscosity with 2% lime added before starch - | | | | | | |
| measurement after: preparation | 2080 | 1010 | 11000 | 5310 | 1130 | 6400 |
| 24 hours rest | 2880 | 1720 | 9880 | 5750 | 210 | 7340 |
| Viscosity with 2% lime added after starch - | | | | | | |
| measurement after: preparation | 8460 | 550 | 8600 | 7000 | 6560 | 6240 |
| 24 hours rest | 7240 | 616 | 8620 | 9300 | 454 | 9940 |

TABLE 14

Effect of shear on the Brookfield viscosities (mPa.s) at 20° C. and 20 rpm.

| | Product | | | | | |
|---|---|---|---|---|---|---|
| | A | C | I | E | J | M |
| Characteristics | | | | | | |
| base | — | — | AP | AP | AP | WM |
| MS | — | — | 0.6 | 0.6 | 0.2 | 0.6 |
| % ECH | — | — | — | 0.025 | 0.025 | 0.02 |
| Concentration | 3.5% | 6.3% | 3.5% | 3.3% | 4.0% | 4.0% |
| Viscosity before shear | 4670 | 5260 | 5060 | 4560 | 5000 | 4600 |
| Viscosity after 30 mn shear at 1500 rpm | 3450 | 3550 | 2460 | 2020 | 1870 | 2400 |
| Viscosity after 30 mn shear and 24 hours rest | 4640 | 4230 | 4120 | 2720 | 2030 | 3640 |
| Ratio viscosity after shear/initial viscosity | 0.74 | 0.67 | 0.55 | 0.44 | 0.37 | 0.52 |
| Ratio viscosity after shear and rest/initial viscosity | 0.99 | 0.80 | 0.78 | 0.60 | 0.41 | 0.79 |

TABLE 15

Brookfield vicosities (mPa · s) at 20° C.) of preparations in tap water as function of the concentration.

| Concentration | | Product A | Product E | Product F | Product G |
|---|---|---|---|---|---|
| 2.0% | 10 rpm | 470 | 312 | 300 | 138 |
| | 20 rpm | 390 | 220 | 220 | 114 |
| | 50 rpm | 290 | 148 | 148 | 89 |
| 3.0% | 10 rpm | 3040 | 3600 | 3430 | 2550 |
| | 20 rpm | 2320 | 2420 | 2280 | 1680 |
| | 50 rpm | 1470 | 1430 | 1330 | 1050 |
| 3.3% | 10 rpm | | 6930 | | |
| | 20 rpm | | 4500 | | |
| | 50 rpm | | 2430 | | |
| 3.5% | 10 rpm | 6960 | 8740 | 7920 | 6400 |
| | 20 rpm | 4670 | 5700 | 5000 | 4160 |
| | 50 rpm | 3000 | 3240 | 2800 | 2360 |
| 3.6% | 10 rpm | | | | 7800 |
| | 20 rpm | | | | 5070 |
| | 50 rpm | | | | 2850 |
| 4.0% | 10 rpm | 15880 | 10780 | 11560 | 10480 |
| | 20 rpm | 6960 | 6900 | 7220 | 6720 |
| | 50 rpm | 4670 | 3850 | 4000 | 3740 |
| 5.0% | 10 rpm | 37200 | 15960 | 19800 | 24500 |
| | 20 rpm | 23250 | 10600 | 12400 | 15280 |
| | 50 rpm | 12300 | 5670 | 6760 | 8280 |

TABLE 16

Stability to ageing of the preparations in tap water - Brookfield viscosities (mPa · s) at 20° C. and 20 rpm.

| Concentration | Product E (0.025% ECH) | Product F (0.033% ECH) | Product G (0.050% ECH) |
|---|---|---|---|
| 2.0% | | | |
| after prep. | 220 | 220 | 114 |
| after 24 h | 400 | 354 | 284 |
| 3.0% | | | |
| after prep. | 2420 | 2280 | 1680 |
| after 24 h | 2720 | 2480 | 2060 |
| 4.0% | | | |
| after prep. | 6900 | 7220 | 6720 |
| after 24 h | 6460 | 7500 | 7060 |
| 5.0% | | | |
| after prep. | 10600 | 12400 | 15280 |
| after 24 h | 8300 | 11450 | 14420 |

TABLE 17

Ford cup 4 and Brookfield viscosities of depilation paints (mPa.s) at 20° C. Comparison with products A and C.

| | Product A | | Product C | | Product E | | Product F | | Product G | |
|---|---|---|---|---|---|---|---|---|---|---|
| Concentration | 1.5% | 2.0% | 1.5% | 2.0% | 1.5% | 2.0% | 1.5% | 2.0% | 1.5% | 2.0% |
| Measurements after preparation | | | | | | | | | | |
| Ford cup 4 (s) | 11.6 | 13.3 | 11.7 | 13.1 | 13.3 | 20.5 | 13.4 | 20.1 | 12.8 | 16.3 |
| Brookfield | | | | | | | | | | |
| 10 rpm | 99 | 308 | 190 | 390 | 224 | 728 | 306 | 668 | 179 | 453 |
| 20 rpm | 75 | 197 | 116 | 234 | 161 | 517 | 204 | 476 | 127 | 318 |
| 50 rpm | 60 | 117 | 67 | 125 | 114 | 334 | 132 | 315 | 87 | 207 |
| 100 rpm | 51 | 93 | 58 | 92 | 101 | 246 | 108 | 232 | 81 | 162 |
| Measurements after 4 hours | | | | | | | | | | |
| Ford cup 4 (s) | 11.6 | 13.3 | 11.7 | 13.1 | 13.3 | 20.0 | 13.5 | 19.4 | 12.6 | 16.1 |
| Brookfield | | | | | | | | | | |
| 10 rpm | 92 | 304 | 190 | 367 | 202 | 657 | 274 | 626 | 161 | 393 |
| 20 rpm | 70 | 195 | 118 | 227 | 148 | 481 | 190 | 456 | 116 | 294 |
| 50 rpm | 58 | 117 | 68 | 127 | 107 | 322 | 123 | 308 | 85 | 201 |
| 100 rpm | 51 | 93 | 55 | 93 | 96 | 241 | 102 | 227 | 80 | 159 |
| Measurements after 24 hours | | | | | | | | | | |
| Ford cup 4 (s) | 11.7 | 13.4 | 11.7 | 13.4 | 13.3 | 20.0 | 13.6 | 19.5 | 12.6 | 16.2 |

TABLE 17-continued

Ford cup 4 and Brookfield viscosities of depilation paints
(mPa.s) at 20° C. Comparison with products A and C.

| | Product | | | | | | | | | |
|---|---|---|---|---|---|---|---|---|---|---|
| | A | | C | | E | | F | | G | |
| | Concentration | | | | | | | | | |
| | 1.5% | 2.0% | 1.5% | 2.0% | 1.5% | 2.0% | 1.5% | 2.0% | 1.5% | 2.0% |
| Brookfield | | | | | | | | | | |
| 10 rpm | 95 | 308 | 193 | 384 | 200 | 639 | 264 | 616 | 155 | 382 |
| 20 rpm | 73 | 202 | 120 | 250 | 151 | 474 | 186 | 450 | 113 | 286 |
| 50 rpm | 60 | 122 | 69 | 140 | 112 | 321 | 119 | 308 | 84 | 199 |
| 100 rpm | 51 | 94 | 57 | 108 | 100 | 237 | 101 | 226 | 79 | 158 |

TABLE 18

Swelling in tap water, in water alkalinized with 2% lime,
and in water containing 2% lime + 14% sodium sulphide.

| | | | Swelling | | |
|---|---|---|---|---|---|
| Product | Medium | Concen-tration | Peak time | Peak viscosity | Viscosity after 15 min |
| A | TW | 4% | ≧15' | — | 152 |
|   | AW | 4% | ≧15' | — | 42 |
|   | SW | 4% | ≧15' | — | 62 |
| B | TW | 7% | ≧15' | — | 71 |
|   | AW | 7% | nm | nm | nm |
|   | AW | 4% | 0'45" | 30 | 19 |
|   | SW | 4% | ≧15' | — | 11 |
| C | TW | 6% | 4 | 89 | 82 |
|   | AW | 6% | 1'55" | 42 | 29 |
|   | SW | 6% | nm | nm | nm |
|   | SW | 4% | 3'00" | 71 | 58 |
| E | TW | 4% | 4'55" | 136 | 92 |
|   | AW | 4% | 5'00" | 160 | 115 |
|   | SW | 4% | 5'20" | 109 | 95 |
| F | TW | 4% | 4'15" | 115 | 91 |
|   | AW | 4% | 3'30" | 163 | 125 |
|   | SW | 4% | 3'00" | 154 | 125 |
| G | TW | 4% | 4'25" | 108 | 93 |
|   | AW | 4% | 4'30" | 160 | 136 |
|   | SW | 4% | 3'40" | 187 | 153 |

TW = tap water
AW = water alkalinized with 2% lime
SW = water containing 2% lime and 14% sodium sulphide
nm = not measurable

TABLE 19

Effect of lime on the Brookfield viscosities
(mPa · s) at 20° C. and 20 rpm.

| Product | A | E | F | G |
|---|---|---|---|---|
| Concentration | 3.5% | 3.3% | 3.5% | 3.6% |
| Viscosity without lime | 4670 | 4560 | 5000 | 5120 |
| Viscosity with 2% lime added before starch - measurement after: | | | | |
| preparation | 2080 | 5310 | 8140 | 10260 |
| 24 hours rest | 2880 | 5750 | 8960 | 11000 |
| Viscosity with 2% lime added after starch - | | | | |

TABLE 19-continued

Effect of lime on the Brookfield viscosities
(mPa · s) at 20° C. and 20 rpm.

| Product | A | E | F | G |
|---|---|---|---|---|
| measurement after: | | | | |
| preparation | 8460 | 7000 | 9040 | 10560 |
| 24 hours rest | 7240 | 9300 | 9940 | 11200 |

TABLE 20

Effect of shear on the Brookfield viscosities
(mPa · s) at 20° C. and 20 rpm.

| Product | A | E | F | G |
|---|---|---|---|---|
| Concentration | 3.5% | 3.3% | 3.5% | 3.6% |
| Viscosity before shear | 4670 | 4560 | 5000 | 5120 |
| Viscosity after 30 mn shear at 1500 rpm | 3450 | 2020 | 3000 | 3160 |
| Viscosity after 30 mn shear and 24 hours rest | 4640 | 2720 | 4060 | 4180 |
| Ratio viscosity after shear/initial viscosity | 0.74 | 0.44 | 0.60 | 0.62 |
| Ratio viscosity after shear and rest/initial viscosity | 0.99 | 0.60 | 0.81 | 0.82 |

TABLE 21

Ford cup 4 and Brookfield viscosities at 20° C.
in a depilation paint for quick-pull system.

| Product | A | F |
|---|---|---|
| Concentration | 2.2% | 1.5% |
| pH | 12.6 | 12.6 |
| Measurements after preparation | 14.1 | 14.0 |
| Ford cup 4 (second) | | |
| Brookfield (mPa · s) | | |
| 10 rpm | 420 | 448 |
| 20 rpm | 262 | 270 |
| 50 rpm | 146 | 148 |
| 100 rpm | 107 | 108 |

TABLE 22

Viscosities at 20° C. and speed of migration in a depilation paint for long-pull system.

| | Product | | | | | | |
|---|---|---|---|---|---|---|---|
| | A | B | C | H | L | Q | N |
| Characteristics | | | | | | | |
| base | PS | PS | PS | PS | PS | PS | PS |
| MS | 0.7 | 0.8 | 0.14 | 0.6 | 0.2 | 0.2 | 0.6 |
| % ECH | 0.02 | 0.08 | 0.025 | 0.10 | 0.05 | 0.19 | 0.03 |
| Concentration (%) | 2.0 | 2.0 | 2.0 | 1.5 | 1.5 | 1.5 | 2.0 |
| Viscosity | | | | | | | |
| Ford cup 4 (second) | 13.5 | 11.2 | 13.7 | 13.8 | 12.9 | 13.6 | 14.8 |
| Brookield (mpa.s) | | | | | | | |
| 10 rpm | 432 | 23 | 660 | 708 | 672 | 828 | 312 |
| 20 rpm | 270 | 24 | 400 | 422 | 388 | 494 | 224 |
| 50 rpm | 148 | 25 | 208 | 222 | 192 | 246 | 147 |
| 100 rpm | 101 | 27 | 135 | 141 | 111 | 151 | 122 |
| Migration test (*) -weight of absorbed liquid (g) after: | | | | | | | |
| 15 mn | — | 15.4 | 13.3 | — | 5.2 | 14.4 | — |
| 30 mn | 0.1 | — | 16.0 | 5.2 | 7.0 | — | 0.1 |
| 60 mn | 0.3 | — | — | 7.8 | 8.6 | — | 0.4 |

(*): the maximum capacity of liquid absorption of the used paper-filter is about 17–18 g.

What is claimed is:

1. A depilatory paint thickener comprising a starch derived from a starch comprising from 95 to 100% amylopectin molecules.

2. A depilatory paint thickener according to claim 1 wherein said starch is obtained from tubers or roots, which are genetically modified so that said starch contains essentially only amylopectin molecules.

3. A depilatory paint thickener according to claim 1 wherein said starch is derived from a plant, which is genetically modified so that said starch contains essentially only amylopectin molecules.

4. A depilatory paint thickener according to claim 3 wherein said plant is a potato.

5. A depilatory paint thickener according to claim 1 wherein said starch is a cross-linked starch.

6. A depilatory paint thickener according to claim 1 wherein said starch is a stabilised starch.

7. A depilatory paint thickener according to claim 1 wherein said starch is an instant starch.

8. A depilatory paint comprising a thickener according to claim 1.

9. A method for depilating an animal hide or skin comprising treating said hide or skin with a depilatory paint according to claim 8.

10. A depilated hide or skin produced by a method according to claim 9.

11. A leather or leather product comprising a depilated hide or skin according to claim 10.

12. A wool comprising a hide or skin treated by a method according to claim 9.

13. A depilatory paint thickener according to claim 1 wherein said starch is an epichlorohydrin cross-linked starch.

14. A depilatory paint thickener according to claim 1 wherein said starch is a hydroxylated starch.

* * * * *

UNITED STATES PATENT AND TRADEMARK OFFICE
CERTIFICATE OF CORRECTION

PATENT NO.   : 6,589,293 B1                                    Page 1 of 1
DATED        : July 8, 2003
INVENTOR(S)  : Guns et al.

It is certified that error appears in the above-identified patent and that said Letters Patent is hereby corrected as shown below:

Title page,
Item [74], now reads "*Attorney, Agent or Firm*: Hoffman & Baron, LLP"
should read -- *Attorney, Agent, or Firm*: Hoffmann & Baron, LLP --

Column 3,
Line 46, now reads "SUMMARY OF THE INVENTION" should read -- DETAILED DESCRIPTION OF THE INVENTION --

Column 9,
Line 16, now reads "The B products B, O and P based on potato starch have a" should read -- The 3 products B, O and P based on potato starch have a --

Column 13,
Line 60, now reads "concentration of it 4.0%. Below 4.0%, the less crosslinked" should read -- concentration of 4.0%. Below 4.0%, the less crosslinked --

Column 23,
Line 55, now reads "H   APS   0.6   o.1   S.o   16100   15800" should read
-- H   APS   0.6   0.1   5.0   16100   15800 --
Line 63, now reads "N   WMS   0.6   0.03   5.0   B5BO   7500" should read
-- N   WMS   0.6   0.03   5.0   858O   7500 --

Signed and Sealed this

Seventh Day of October, 2003

JAMES E. ROGAN
*Director of the United States Patent and Trademark Office*